US008845948B2

(12) United States Patent
Ikuta et al.

(10) Patent No.: US 8,845,948 B2
(45) Date of Patent: Sep. 30, 2014

(54) CYTOCOMPATIBLE THREE-DIMENSIONAL STRUCTURES FABRICATED BY MICROSTEREOLITHOGRAPHY

(75) Inventors: Koji Ikuta, Aichi (JP); Yoshinori Inoue, Aichi (JP)

(73) Assignee: Japan Science and Technology Agency, Saitama (JP)

( * ) Notice: Subject to any disclaimer, the term of this patent is extended or adjusted under 35 U.S.C. 154(b) by 509 days.

(21) Appl. No.: 12/998,553

(22) PCT Filed: Oct. 26, 2009

(86) PCT No.: PCT/JP2009/068734
§ 371 (c)(1),
(2), (4) Date: Jul. 15, 2011

(87) PCT Pub. No.: WO2010/050604
PCT Pub. Date: May 6, 2010

(65) Prior Publication Data
US 2011/0268948 A1    Nov. 3, 2011

(30) Foreign Application Priority Data
Oct. 30, 2008  (JP) ................ 2008-279411

(51) Int. Cl.
| | |
|---|---|
| B29C 35/08 | (2006.01) |
| B29C 41/02 | (2006.01) |
| B29C 71/02 | (2006.01) |
| C12M 1/00 | (2006.01) |
| B29C 67/00 | (2006.01) |
| B29L 31/00 | (2006.01) |
| B29C 71/04 | (2006.01) |

(52) U.S. Cl.
CPC ............ *B29C 67/0066* (2013.01); *C12M 23/20* (2013.01); *B29L 2031/7532* (2013.01); *B29C 71/02* (2013.01); *B29K 2995/0094* (2013.01); *B29C 2035/0827* (2013.01); *B29C 67/0085* (2013.01); *B29C 71/04* (2013.01)
USPC .......................................... 264/401; 264/234

(58) Field of Classification Search
USPC ................................ 264/232, 234, 236, 401
See application file for complete search history.

(56) References Cited

U.S. PATENT DOCUMENTS

| | | | | |
|---|---|---|---|---|
| 5,731,388 | A | * | 3/1998 | Suzuki et al. ................. 525/404 |
| 5,807,519 | A | * | 9/1998 | Suzuki et al. ................. 264/401 |
| 6,660,208 | B2 | * | 12/2003 | Hanna ........................... 264/401 |

FOREIGN PATENT DOCUMENTS

JP        2003-10312 A      1/2003

OTHER PUBLICATIONS

Seung-Jea Lee et al., "Development of a scaffold fabrication system using an axiomatic approach", Journal of Micromechanics and Microengneeing, vol. 17, pp. 147-153, IOP Publishing Ltd., 2007.

(Continued)

*Primary Examiner* — Leo B Tentoni
(74) *Attorney, Agent, or Firm* — Rader, Fishman & Grauer PLLC

(57) ABSTRACT

Three-dimensional microstereolithographic objects fabricated by microstereolithography are exposed to UV light for one hour to accelerate hardening. The structures are then heated at 175° C. or above for at least 6 hours. The heating temperature may exceed the glass transition temperature, which is the index of thermal softening temperature of materials. The present invention relates to three-dimensional microstructures formed by microstereolithography. Deformation due to a structure's own weight, which generally poses a problem in heat treatment, is reduced with microstructures due to the size effect. As a result, the dimensions of the three-dimensional structure fabricated by the present invention remain almost unchanged before and after the heat treatment.

2 Claims, 4 Drawing Sheets

(56) References Cited

OTHER PUBLICATIONS

Koji Ikuta et al., "Micro Hikari Zokeiho eno Saibo Tekigosei Fuyo Process no Kaihatsu", vol. 10, No. 4, pp. 507-512, Nippon Computer Geka Gakkaishi, Dec. 30, 2008.

Koji Ikuta, "Micro Hikai Zokeiho Zokeiho no Shinten to Biomedical Oyo", pp. 47-48, The Japan Society of Mechanical Engineers Kanto Shibu Dai 8 Ki Sokai Koenkai Koen Ronbunshu, 2002.

Ikuta et al., "Real Three Dimensional Micro Fabricating using Stereo Lithography and Metal Molding", Kyushu Institute of Technology, pp. 42-47, IEEE International Worksho on Micro electro Mechanical Systems, 1993.

Bertsch et al., "Microstereolithography", pp. 2-15, Mat. Res. Soc. Symp. Proc. vol. 758, Materials Research Society, 2003.

Maruo et al., "Submicron Manipulation Tools Driven by Light in a Liquid", Applied Physics Letter, vol. 82, No. 1, pp. 133-135, American Institute of Physics, 2003.

Kawata et al., "Finer Features for Functional Microdevices", Nature, vol. 412, pp. 697-698, Macmillan Magazines Ltd., 2001.

Maruo et al., "Submicron Stereolithograpy for the Production of Freely Movable Mechanisms by using Single-Photon Polymerization", Nagoya University, pp. 70-76, Elsevier Science B.V., 2002.

Chen, "Micro and Naon-Fabrication of Biodegradable Polymers for Drug Delivery", The University of Texas, pp. 1621-1633, Elsevier B.V., 2004.

Tsang, et al.; Three-Dimensional Tissue Fabrication, University of California, pp. 1636-1647, Elsevier B.V., 2004.

Popov et al., "Laser Stereolithography and Supercritical Fluid Processing for Custom-Designed Implant Fabrication", Journal of Materials Science Materials in Medicine 15, pp. 123-128, Kluwer Academic Publishers, 2004.

Lee et al., "3D Scaffold Fabrication with PPF/DFF using Micro-Stereolithography", Science Direct, Microelectronic Engineering 84, pp. 1702-1705, Elsevier B.V., 2007.

Matsuda et al., "Liquid Acrylate-Endcapped Biodegrable Poly($\epsilon$-Caprolactone-co-trimethylene Carbonate).II.Computer-Adided Stereolithographic Microarchitectureal Surface Photoconstructs", J. Bomed Mater Res., pp. 395-403, Wiley Periodicals, Inc., 2002.

Lee et al., "Poly(propylene fumarate) Bone Tissue Engineering Scaffold Fabrication using Stereolithography; Effects of Resin Formulations and Laser Parameters", Biomacromolecules, pp. 1077-1084, American Chemical Society, 2007.

Cooke et al., "Use of Stereolithography to Manufacture Critical-Sized 3D Biodegradable Scaffolds for Bone Ingrowths", J. Biomed Mater Res Part B. Appl Biomater, pp. 65-69, Wiley Periodicals, Inc., 2002.

Arcaute et al., "Stereolithography of Three-Dimensional Bioactive Poly(Ethylene Glycol) Constructs with Encapsulated Cells", Annals of Biomedical Engineering, vol. 34. No. 9, pp. 1429-1441, 2006.

Lee et al., "Development of a Scaffold Fabrication System using an Axiomatic approach", Journal of Micromechanics and Microengineering, pp. 147-153, Institute of Physics Publishing, 2007.

Jones et al., "Copper induced oxidation of serotonin: analysis of products and toxicity", Journal of Neurochemistry, International Society of Neurochemistry, vol. 7, pp. 1035-1043, Journal Compilation, 2007.

International Search Report mailed on Jan. 19, 2010.

\* cited by examiner

FIG. 4

Experimental parameters of postcure processes

| | Resin type | Fabrication method | Post-Exposure | Post-Cure Post-Bake Temperature(°C) | Time(hour) | Ultraviolet Spectrometry |
|---|---|---|---|---|---|---|
| 1 | SCR751 | stereolithography | | R.T. | | O |
| 2 | SCR751 | stereolithography | O | R.T. | | |
| 3 | SCR751 | stereolithography | O | 150 | 0.5 | |
| 4 | SCR751 | stereolithography | O | 150 | 3 | |
| 5 | SCR751 | stereolithography | O | 150 | 6 | |
| 6 | SCR751 | stereolithography | O | 150 | 9 | |
| 7 | SCR751 | stereolithography | O | 150 | 12 | |
| 8 | SCR751 | stereolithography | O | 150 | 24 | |
| 9 | SCR751 | stereolithography | O | 175 | 0.5 | |
| 10 | SCR751 | stereolithography | O | 175 | 3 | |
| 11 | SCR751 | stereolithography | O | 175 | 6 | |
| 12 | SCR751 | stereolithography | O | 175 | 9 | |
| 13 | SCR751 | stereolithography | O | 175 | 12 | |
| 14 | SCR751 | stereolithography | O | 175 | 24 | |
| 15 | SCR751 | stereolithography | O | 200 | 0.5 | |
| 16 | SCR751 | stereolithography | O | 200 | 3 | |
| 17 | SCR751 | stereolithography | O | 200 | 6 | O |
| 18 | SCR751 | stereolithography | O | 200 | 9 | |
| 19 | SCR751 | stereolithography | O | 200 | 12 | |
| 20 | SCR751 | stereolithography | O | 200 | 24 | |
| 21 | SCR751 | Xe lamp & casting | | R.T. | | |
| 22 | SCR751 | Xe lamp & casting | | 200 | 6 | |
| 23 | SCR701 | Xe lamp & casting | | R.T. | | |
| 24 | SCR701 | Xe lamp & casting | | 200 | 6 | |
| 25 | SCR11120 | Xe lamp & casting | | R.T. | | |
| 26 | SCR11120 | Xe lamp & casting | | 200 | 6 | |

FIG. 5

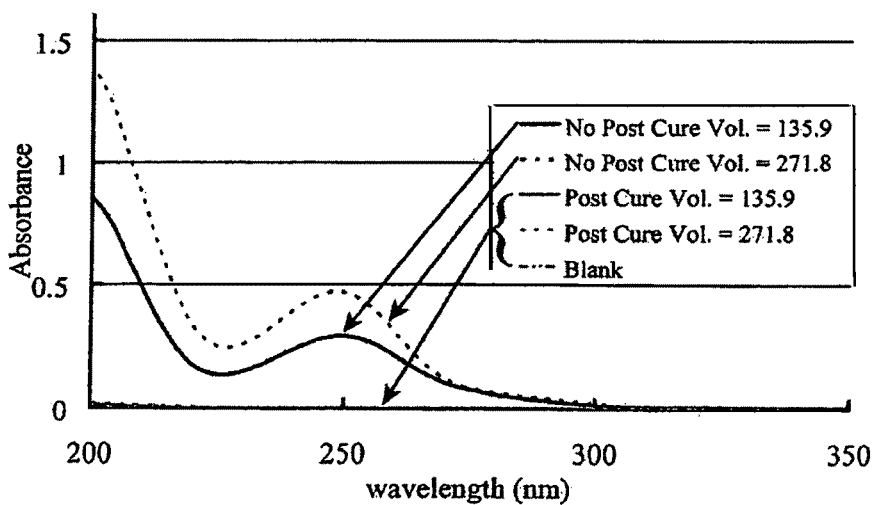

Ultraviolet absorption spectrum

CYTOCOMPATIBLE THREE-DIMENSIONAL STRUCTURES FABRICATED BY MICROSTEREOLITHOGRAPHY

FIELD OF TECHNOLOGY

The present invention relates to the fabrication of free-form solid objects by Microstereolithography, the photocurable materials used therein, and the technology to render materials cytocompatible. The present invention in particular relates to objects that are nontoxic, in terms of cytocompatibility, while remaining in contact with isolated cells for long periods.

BACKGROUND TECHNOLOGY

Microstereolithography is a precision machining technology to fabricate structures of an arbitrary shape by exposing photocurable resins to laser light. In 1992, Ikuta et al., the inventors of the present invention, achieved the world's first 5 μm three-dimensional resolutions (Non-patent Literature 1). Many research studies followed and papers were published after the announcement (Non-patent Literature 2). Nano-stereolithography at sub-micro resolutions has also been developed. Recently, microstereolithography is being applied to μ-TAS for studying and analyzing chemical reactions occurring in microchannels, and to the development of MEMS devices (Non-patent Literature 3-5).

But commercial photocurable resins do not have biocompatibility, so microstereolithography has not been applied to devices that need to be in direct contact with cells or living organisms (Non-patent Literature 6-8).

To solve this problem, the inventors of the present invention decided to develop a new post process to add cytocompatibility to commercial microstereolithographic epoxy photocurable resins which already have proven stable photocurable and other characteristics. They chose this approach as it is more versatile and applicative than trying to develop new photocurable resins with the required biocompatibility, curing characteristics and accuracy.

So far, the following reports have introduced the application of microstereolithography to devices that are indirect contact with living cells or organs:

Firstly, photo initiators, which are highly cytotoxic materials, are avoided and biodegradable polymers, for example caprolactone or poly (propylene fumarate), are adopted to synthesize new photocurable resins for microstereolithography (Non-patent literature 8-11). This approach necessitates a resin synthesis and blending process. Furthermore, the approach is designed to fabricate biodegradable scaffolds for cells in tissue engineering. As such, this approach cannot be used to fabricate non-degradable devices to be used in the present invention.

Secondly, hydrogels such as polyethylene glycol are used in microstereolithography to fabricate scaffolds for cells (Non-patent Literature 7 and 13). It is possible to culture cells on hydrogel surfaces and inside hydrogels, but this method is difficult to apply to the fabrication of devices because of the insufficient strength of the hydrogels.

Furthermore, low processing accuracy due to desiccation shrinkage is a large problem, and this approach does not meet the objectives of our present research.

Thirdly, cell culturing on the surfaces of three-dimensional lattice structures made of commercial photocurable resins has been reported, however cell cultures on planar structures failed (Non-patent Literature 14).

1) Non-patent Literature: Ikuta K, Hirowatari K, Real three-dimensional microfabrication using stereo lithography and metal molding. Proceedings of the IEEE Workshop on Microelectromechanical Systems, MEMS' 93. 1993: 42-47.

2) Non-patent Literature: Bertsch A, Jiguet S, Bernhard P, Renaud P, Microstereolithography: a Review. Mat. Res. Soc. Symp. Proc. 2003, OO1.1.1-LL1.1.13

3) Non-patent Literature: Maruo S, Ikuta K, Korogi H. Submicron manipulation tools driven by light in a liquid. Appl Phys Lett 2003; 82: 133-135

4) Non-patent Literature: Kawata S, Sun HB, Tanaka T, Takada K. Finer features for functional microdevices. Nature 2001; 412: 697-698

5) Non-patent Literature: Maruo S, Ikuta K. Submicron stereolithography for the production of freely movable mechanism by using single-photon polymerization. Sensor Actuat A-phys 2002; 100: 70-76

6) Non-patent Literature: Lu, Chen SC. Micro and nano-fabrication of biodegradable polymers for drug delivery. Adv Drug Deliv Rev. 2004; 11: 1621-33

7) Non-patent Literature: Tsang VL, Bhatia S N. Three-dimensional tissue fabrication. Adv Drug Deliv Rev. 2004; 11: 1635-47

8) Non-patent Literature: Popov VK, Evseev AV, Ivanov A L, Roginski VV, Volozhin AI, Howdle SM. Laser stereolithography and supercritical fluid processing for custom-designed implant fabrication. J Mater Sci Mater Med. 2004; 2: 123-8

9) Non-patent Literature: Lee JW, Lan PX, Kim B, Lim G, Cho DW. 3D scaffold fabrication with PPF/DEF using macro-stereolithography. Microelectron Eng 2007; 84: 1702-1705

10) Non-patent Literature: Matsuda T, Mizutani M. Liquid acrylate-endcapped biodegradable poly(e-caprolacton-co-trimethyrene carbonate). II. Computer-aided stereolithographic microarchitectual surface photoconstructs. J Biomed Mater Res. 2002; 3: 395-403

11) Non-patent Literature: Lee KW, Wang S, Fox BC, Ritman E L, Yaszemski MJ, Lu L. Poly (propylene fumarate) bone tissue engineering scaffold fabrication using stereolithography: effects of resin formulations and laser parameters. Biomacromolecules. 2007; 4: 1077-84

12) Non-patent Literature: Cooke MN, Fisher JP, Dean D, Rimnac C, Mikos AG. Use of stereolithography to manufacture critical-sized 3D biodegradable scaffolds for bone ingrowth. J Biomed Mater Res B Appl Biomater. 2003; 2: 65-9

13) Non-patent Literature: Arcaute K, Mann BK, Wicker R B. Stereolithography of Three-Dimensional Bioactive Poly (Ethylene Glycol) Constructs with Encapsulated Cells. Ann Biomed Eng 2006; 34; 1429-1441

14) Non-patent Literature: Lee SJ, Kang HW, Kang TY, Kim B, Lim G, Rhie JW, Cho DW, Development of scaffold fabrication system using an axiomatic approach. J Micromech Microeng 2007; 17: 147-153

15) Non-patent Literature: Jones CE, Underwood CK, Coulson EJ, Taylor PJ. Copper induced oxidation of serotonin: analysis of products and toxicity. J Neurochem 2007; 102: 1035-1043

DISCLOSURE OF INVENTION

Problems to be Resolved by the Invention

Three-dimensional structures fabricated by conventional microstereolithography have been known to exhibit, as described above, cytotoxicity due to non-uniform reaction and hardening, and due to the effects of monomers, oligomers, photo-polymerization initiators, free radicals, polyol, and stabilizers remaining in the photo curing materials (Patent Literature 1).

Many biodegradable materials have been proposed as biocompatible materials for applications where the end product contacts the living body for a long time (Patent Literature 2 and Non-patent literature 10 and 12). Conventional technologies have placed emphasis on manufacturing nontoxic materials rather than detoxifying existing materials. Research has been conducted to detoxify three-dimensional structures fabricated by microstereolithography by adding a post process to the product (Patent Literature 1). The product has biocompatibility at least when in contact with the skin and can be used for a long period of time while in direct contact with the skin.

[Patent Literature 1] Publication of unexamined patent application No. 10312-2003

[Patent Literature 2] Publication of unexamined patent application No. 284550-2007

From above previous reports, the inventors of the present invention have estimated that uncured monomers and photopolymerization initiators remaining in the microstereolithographic object are responsible for the cytotoxicity of the microstereolithographic object. The inventors therefore investigated various post-curing processes (promoting polymerization and curing of uncured monomers after microstereolithography) to promote polymerization of the uncured monomers and suppress the effect of the photopolymerization initiators eventually to reduce the cytotoxicity of the microstereolithographic object.

Three-dimensional structures formed by microstereolithography have a limited range of applications due to their inherent cytotoxicity. When any toxic materials are to be used in the production of devices that may be in contact with the human body, a process to detoxify the materials must be added. The addition of such a process, however, is industrially more favorable than newly developing a nontoxic photocuring material because conventional materials, even though they may be toxic, have proven three-dimensional processing accuracy.

In consideration of the above factors, the objective of the present invention is to detoxify three-dimensional structures fabricated by microstereolithography and provide cytocompatible three-dimensional structures. Cytocompatibility is a property of a material which means that the material is nontoxic to cells and does not have an adverse effect on the activities of living cells.

Means to Solve the Problems

With a view to solving these conventional problems, the present invention has an objective to provide minute three-dimensional structures fabricated by microstereolithography, wherein said structure is detoxified and is cytocompatible at least to the extent that cells isolated and cultured outside living organisms can be cultured on the surface of and in contact with said structure; and that said detoxification is achieved by heating said structure to at least its glass transition temperature after UV-curing.

The structures are mainly formed from photocuring materials selected from the group of acrylate, epoxy, acrylate-epoxy complex, and oxetane.

The above glass transition temperature is about 175 to 200° C., and the heating time is 6 to 24 hours.

One of the dimensions x, y, and z of at least one portion of said structure is less than 1 mm, and deformation of the structure due to its own weight when it is heated above its glass transition temperature is reduced due to the size effect.

Effects of the Invention

It has been confirmed that the three-dimensional structure fabricated by microstereolithography according to the present invention has the same cytocompatibility level as that of commercial cell culture dishes. This invention makes it possible to use three-dimensional structures fabricated by microstereolithography in the production of cytocompatible products.

This technology can be applied to the design of tailor-made implant devices using microstereolithography which had never been possible previously. It further makes it possible for three-dimensionally configured cell devices and microchemical devices, such as chemical IC chips, to be used as cells. This process would become a key technology that substantializes a new approach to biomedical studies.

BRIEF DESCRIPTION OF THE DRAWINGS

FIG. 4 shows the experimental parameters of the post-curing process. These post-curing conditions were used in the Embodiments.

FIG. 5 shows the absorbance spectra of water in which the microstereolithographic objects were immersed for 40 hours. The peaks of the spectra were found at around 249 nm and 200 nm for water in which non-post-cured microstereolithographic objects were immersed. This means that the microstereolithographic objects eluted some substances, and the absorbance spectra of these substances were measured. It was confirmed that the post-cured microstereolithographic objects did not give off substances having such an absorbance spectrum.

EXPLANATION OF THE SYMBOLS

1 UV laser
2 Liquid resins
3 Solid polymer

BEST MODE OF IMPLEMENTING THE INVENTION

Three-dimensional microstereolithographic objects fabricated by microstereolithography were exposed to UV light for one hour to accelerate hardening. The structures were then heated at 175° C. or above for at least 24 hours, or at 200° C. or above for 6 hours. The heating temperature may exceed the glass transition temperature, which is the index of thermal softening temperature for materials. The present invention relates to three-dimensional microstructures formed by microstereolithography. Deformation due to a structure's own weight, which generally poses a problem in heat treatment, is reduced when dealing with microstructures (that is, for example, when one of the dimensions x, y, and z of at least one portion of a structure is less than 1 mm) due to the size effect. As a result, the dimensions of the three-dimensional structure fabricated by the present invention remained almost unchanged before and after heat treatment. We performed cytocompatibility tests on this three-dimensional structure and found that it is cytocompatible.

EMBODIMENTS

Working Examples

Figure 1:
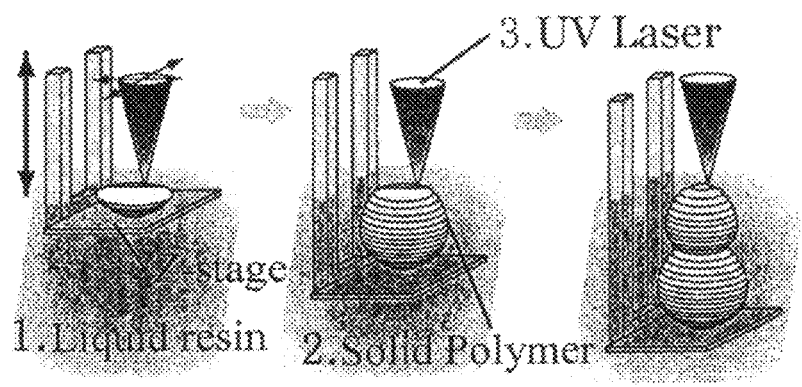
FIG. 1 illustrates the fabrication of a three-dimensional structure by microstereolithography.

<Experiments of Cytocompatibility with Post Cure>
(Materials and Method)
Microstereolithography FIG. 1 shows the procedure used to fabricate three-dimensional structures according to the present invention.

The steps of the microstereolithography procedure are described below.

1. Inputting the 3-D shape model into 3-D CAD based on design data.

2. Converting the 3-D shape model to x-y cross-sectional n slice data perpendicular to the z-axis.

3. Hardening of the photocurable resins using a scanning ultraviolet laser in the x-y plane from the first layer of the slice data.

4. Forming a thin film of the liquid photocurable resins after scanning the laser on the first layer and repeating the process to the nth layer (FIG. 1).

The microstereolithographic objects thus fabricated were washed in glycol ether ester and then in 99.5% ethanol for 3 minutes, respectively, in an ultrasound bath. The microstereolithographic objects were then stored in a desiccator.

In our microstereolithography system, a He—Cd laser (325 nm, Kimmon Koha Co., Ltd.) was used as the light source.

The microstereolithography parameters were laser power, 15 mW; laser scanning speed, 800 mm/sec; scanning distances, 15 μm; and layer thickness, 100 μm.

Cell culture wells were fabricated to evaluate the cytocompatibility of the photocurable resins. The size of the wells were outside diameter, 16 mm; inside diameter, 15 mm; bottom thickness, 0.8 mm; and height of surrounding wall, 2 mm.
Photocurable Resins For the microstereolithography, epoxy-type universal photocurable resins (SCR-751, D-Mec; critical exposure, 20 mj/cm2; glass transition temperature after hardening, 108° C.) were adopted.

For the purpose of studying the characteristics with various resins, we used two other resins in the culture tests in addition to the above universal photocurable resins: epoxy-type universal humidity-resistant photocurable resins (SCR-701, D-Mec; critical exposure, 33 mj/cm2; glass transition temperature after hardening, 81° C.) and epoxy-type water-resistant high toughness photocurable resins (SCR-11120, D-Mec; critical exposure, 12 mj/cm; glass transition temperature, 43° C.). These three types of resins were hardened by the Xenon lamp to use in the cell culture test.

In addition to the above resins, photocuring materials selected from the group of acrylate, epoxy, acrylate-epoxy complex, and oxetane can also be used as photocurable resins.
Cell Culture Rat adrenal pheochromocytoma cell line (PC12, RBC0009, Riken Cell Bank, Tsukuba) was used in the cytocompatibility test because this is the cell line typically used in neurological toxicity tests 15). The cell culture medium was DMEM (MED-006, Iwaki) including 10% fetal bovine serum and 10% horse serum. The cell suspension was adjusted to $5.1 \times 10^2$ cells/mm$_2$, and cultured at 37° C., in a 5% $CO_2$ atmosphere.

The positive controls were cultured in a commercial 96-well Micro Well Plate (3860-096, Iwaki).
Observation, Counting and Evaluation The interiors of the cell culture wells fabricated by microstereolithography were observed using a phase contrast microscope. Micrographs were taken at 3 mm, 4 mm, 5 mm, and 6 mm from center of the well using a CCD camera. Cell morphology was observed and cell density counted from these micrographs. To reduce the effects of initial concentration dispersion, the cell proliferation rate was defined to evaluate the correlation between this rate and the post-curing parameters. The cell proliferation rate y was calculated as the rate of the density of the 48 hour cell culture: y to the initial density of a 1 hour cell culture: x, or $\gamma = y/x \times 100$.
Cytocompatibility Cytocompatibility in this report was defined to be the condition in which cells could proliferate and adhere to the bottom of the wells made of photocurable resins.
Statistics The derived cell proliferation rate data were statistically processed using the student's t-test. It was assumed that there was a significant difference for $\alpha < 0.05$ compared with the positive control. The sample size n was 12.
(Deliberation of Post-Curing Processes)

There are generally two types of post-curing processes used to finish polymerization in microstereolithography. One is the post-exposure process in which the microstructures after microstereolithography are exposed in a mercury lamp, etc. The other is the post-bake process in which the environmental temperature is increased to promote hardening.

In the present study, the cell culture wells, which were fabricated by microstereolithography, were both post-exposed and post-baked (hereafter termed "post-cured"). Specifically, after the structures were exposed with a xenon lamp (L2423, Hamamatsu Photonics) for 1 hour, they were heated in an oven (DRD360DA, Advantec) at respective temperatures (room temperature, 150° C., 175° C., and 200° C.) for respective heating times (0.5, 3, 6, 9, 12, and 24 hours) (FIG. 4). These wells were then exposed in UV light for 1 hour to sterilize them before the cell culture.

The culture plates, which were hardened under a xenon lamp, were post-baked at 200° C. for 6 hours.
(Results of Experiments)

The cell culture wells after the post-exposure and post-bake began browning. Although the wells were transparent pale yellow when they were photo-hardened before the post-bake, the wells became browner and had lower transmittance with higher temperatures or with longer heating times.

The results of the cell culture tests are described below.

1) In the cell culture wells without the post-curing process, almost all of the cells died within 3 hours after cell seeding.

Figure 2:
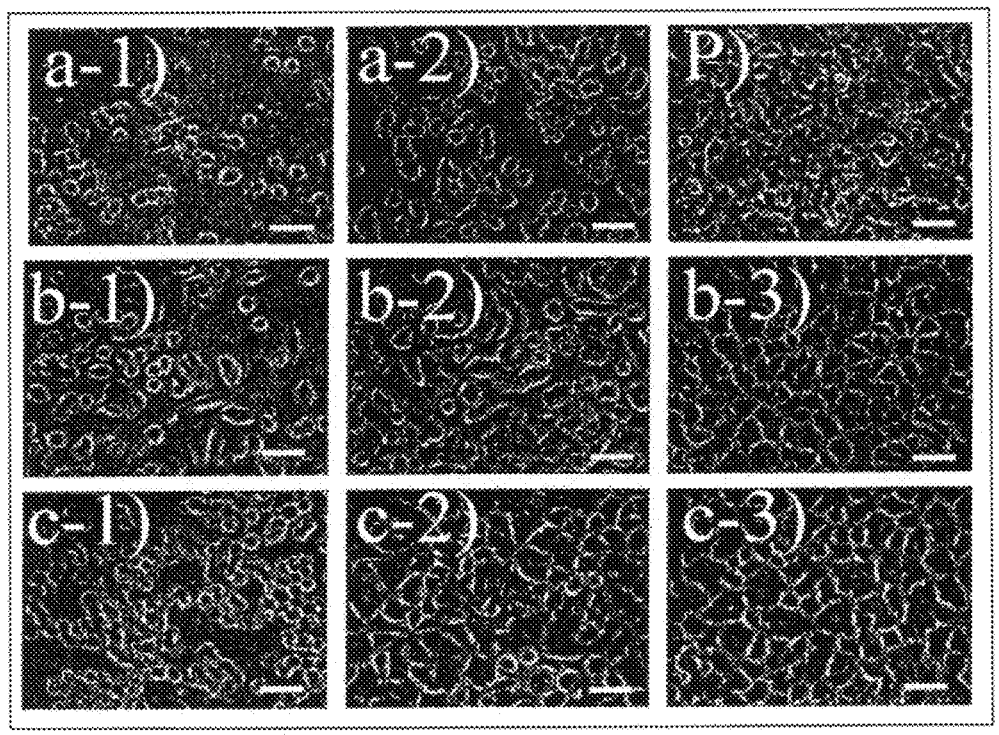
FIG. 2 is a series of phase-contrast micrographs of cells 48 hours after seeding. P shows positive control cells on a commercial cell culture dish. The upper images show cells post-cured at 150° C. for 6 hours (a-1) and 12 hours (a-2). b-1), 2), and 3) show cells post-cured at 175° C. for 6, 12, and 24 hours. c-1), 2), and 3) show cells post-cured at 200° C. for 3, 6, and 12 hours. The cell proliferation rate of b-3), c-2), and c-3) are almost same as the positive controls in statistical data. All bars in the photographs are 50 μm.

2) Surviving cells were confirmed in some post-cured wells depending on the test conditions as shown in FIG. 2. The cells in the positive control condition were confluent in the 48 hour cell culture. The cells in the wells post-cured at 175° C. for 24 hours and those in the wells post-cured at 200° C. for 6 hours or longer were confluent in the same manner (b-3, c-2, and c-3, FIG. 2).

Figure 3A:
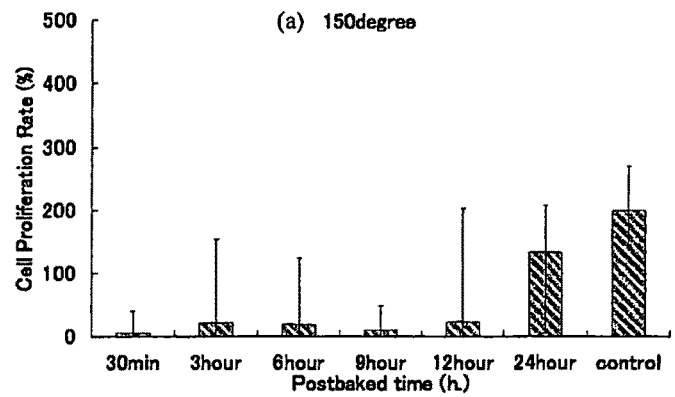
FIG. 3 shows the cell proliferation rate of cells on a post-cured cell culture dish fabricated by microstereolithography with 48 hours of cell culture. Asterisks (*) mean that there is not significant statistical difference compared with positive controls cultured on a commercial cell culture dish (a=0.05).
Figure 3B:
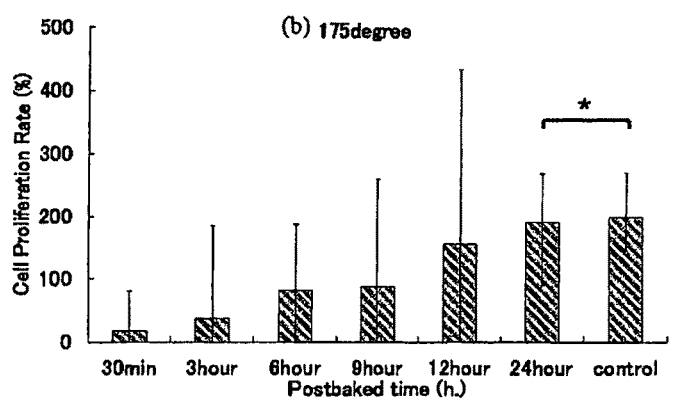
Figure 3C:
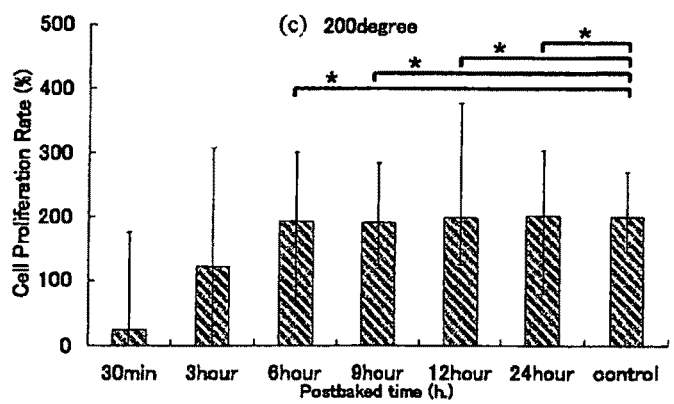

3) In FIG. 3 (a), there was a significant difference in the cell proliferation rate between the positive controls and those post-baked at 150° C.

4) At the 175° C. post-bake temperature, there was no significant difference between the positive control and those after 24 hours of post-bake time although there was significant difference between positive control and those with 12 hours or less post-bake time (FIG. 3 (b)).

5) In FIG. 3 (c), or at the 200° C. post-bake temperature, there was no significant difference in the cell proliferation rate between the positive control and those with 6 hours or more of post-bake time.

The above results show that the optimum post-bake conditions are 200° C. and 6 ours post-bake time to attain the same cell proliferation rate as commercial cell culture dishes with the shortest heating time.

[Verification of Substance Eluted from Photocurable Resins]

We held the hypothesis that removing polymerization initiators from the photocurable resins would be the condition for said resins to achieve cytocompatibility. The above experiments have shown the effectiveness of post-curing to prove this hypothesis, and the relevant necessary conditions. The substance eluted from the photo substances into water is investigated in this chapter to verify the parameters of the post-curing process more precisely.

(Materials and Methods)

The cell culture wells which had 496.8 $mm^2$ surface areas and 135.9 $mm^3$ volumes were fabricated by microstereolithography. The other parameters remained the same as those in the preceding paragraph "Microstereolithography" in page 6. These wells were post-cured at 175° C. or above for at least 24 hours, or at 200° C. or above for 6 hours, which were determined to be the optimum parameters as described in the preceding chapter.

For comparison purposes, post-cured and non-post-cured wells were dipped in 5 ml milliQ water for 40 hours under the condition of one (Vol.=135.9 $mm^3$) and two (Vol.=271.8 $mm^3$) wells at a time, respectively. The absorbance spectra of the milliQ water were measured using a UV absorption spectrophotometer (BioSpec-1600, Shimadzu). The spectra were compensated for the spectrum of the pure water as the base line. The optical path in the measurement was 1 cm long.

(Results of Experiments)

When the hardening of the photocurable resins was actually accelerated by the post-curing process, the elution into water of photopolymerization initiators and uncured monomers, which are assumed to be the cause of cytotoxicity, should be suppressed. Since the conditions for making photocurable resins cytocompatible are determined in the above cytocompatibility tests, we studied the relationship between the post-curing process and elution of substances from photocurable resins into water using ultraviolet absorption spectroscopy. It was confirmed that substances having absorption spectra at around 249 nm and around 200 nm had eluted from the hardened but non-post-baked photocurable resins as shown in FIG. 5. Since the size of the absorbance peak of the absorption spectrum is correlated with the volume of the resins in the solvent, it is thought that these substances eluted from the resins. In contrast, these absorption spectra were not detected from the post-cured photocurable resins.

The temperature of our post-bake process was higher than the glass transition temperature of the photocurable resins. As such, the structures would be deformed due to their own weight if the structures were heavy, or due to the load applied during the post-bake process. But the microstructures fabricated using our microstereolithography method were mostly small in size ranging from few μm to 1 mm. In this size range, the volume force is sufficiently small compared with the surface force due to scale effect, and thermal deformation is small enough to be neglected. Our post-bake process can therefore be applied to microscale objects without restrictions on their geometry.

As discussed above, absorption spectra peaking at around 249 nm and around 200 nm were detected in the water in which non-post-cured photocurable wells were immersed. The absorbance increased with the increasing volume of the photocurable resins, or the concentration of the eluted substances increased (FIG. 5).

In contrast, these two peaks were not detected from the water in which the post-cured photocurable wells were immersed. These results indicate that the eluted substances interfered with the cell proliferation on the photocurable resins and verify our hypothesis and our suggested solutions to be correct.

[General Versatility of Post-Curing Process]

Whether the post-curing process is effective for other photocurable resins was verified by experiments.

(Materials and Methods)

In addition to the above photocurable resins SCR-751, two types of epoxy microstereolithography resins that were the general-purpose epoxy humidity-resistant photocurable resins (SCAR-701, D-Mec; critical exposure, 33 mj/cm2; glass transition temperature after hardening, 81° C.) and water-resistant and high-toughness epoxy photocurable resins (SCR-11120, D-Mec; 12 mj/cm2, 43° C.) were hardened using a xenon lamp for use in the cell culture tests.

Each of the above three photocurable resins was set in a silicone gum mold, and the circular plates of 16 mm in diameter and 0.8 mm in thickness were exposed to a xenon lamp for hardening. The plates were then post-baked at 200° C. for 6 hours for use in the cell culture tests (21-26, FIG. 4). The cell morphology was observed 48 hours after seeding under a phase contrast microscope.

(Results of Experiments)

Figure 6:
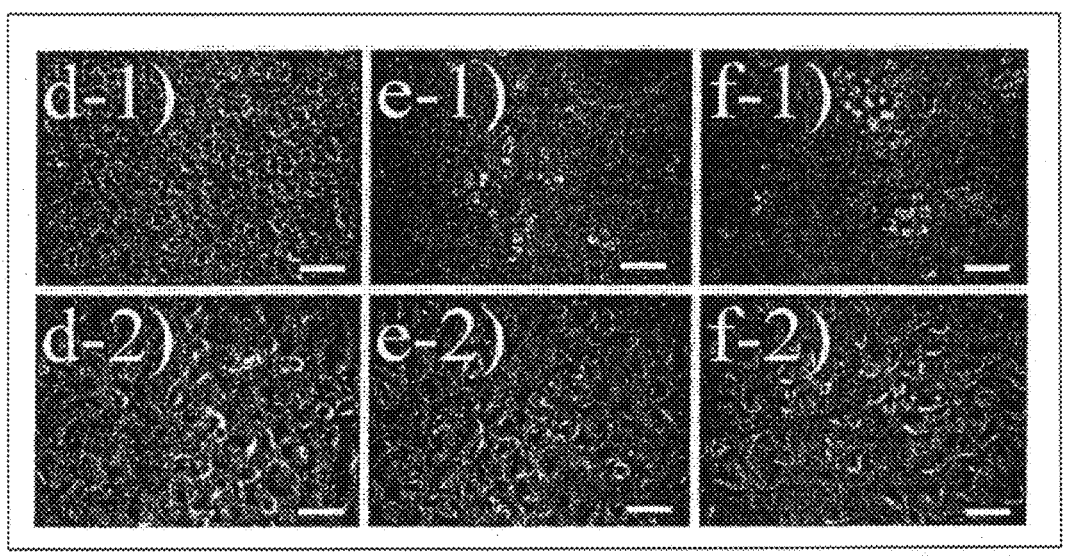
FIG. 6 shows phase-contrast micrographs of cells 48 hours after seeding. To evaluate different photocurable resins, culture tests were conducted for d) SCR751, e) SCR701, and f) SCR11120. Suffix number 1 indicates resins without post-curing and 2 are those with post-cure. It is known from these photos that post-curing is effective for all resin types. All bars in the photos are 50 μm.

When post-curing was not performed, all cells on all plates made of the three photocurable resins did not adhere to the surface of the plate and were dead within hours as shown in FIGS. 6: d-1, e-1, and f-1. In contrast, all cells cultured on the post-cured plates adhered to the surface and were alive as shown in FIGS. 6: d-2, e-2, and f-2. The general versatility of the post-curing process was verified by these results.

Observations

It was discovered that cytocompatibility can be added to epoxy-type photocurable resins by post-curing them at 200° C. for 6 hours. This result was the world's first report that the same level of cell culture directly adhered to photocurable resins and proliferated to cell numbers comparable with commercial polystyrene dishes. The photocurable resins changed to brown and rejected observation of the inside of the wells if post-baked at over 200° C. The shortest post-bake time to add cytocompatibility to the photocurable resins while reducing the color change was 6 hours at 200° C.

Popov et al have reported that cytotoxicity was removed by supercritical carbon dioxide treatment from hydroxyapatite composites fabricated by stereolithography (Non-patent Literature 8). Arcaute et al have reported the relationship between the concentration of the photo-polymerization initiator and cytotoxicity (Non-patent Literature 13). X Lee et al have reported that the geometry of scaffolds fabricated by stereolithography changed cell activities (Non-patent Literature 14). All of these reports, however, do not compare their results with cell activities observed using ordinary cell culture methods, and simply propose one condition to improve the cell culture method. These reports, therefore, cannot compare with our result in which the same level of cytocompatibility as in routinely used cell culture dishes has been achieved.

The above post-bake temperature was higher than the glass transition temperature of the photocurable resins. As such, the structures would be deformed due to their own weight if the structures were heavy, or due to the load applied during the post-bake process, however the microstructures fabricated by our microstereolithography were mostly small in size ranging from few μm to 1 mm.

In this microsize range, the volume force, such as gravity, is small compared with the surface force due to the scale effect, and thermal deformation is greatly reduced in the post-curing process. Our post-bake process can therefore be applied to microscale objects without restrictions on their geometry.

As shown in FIG. 5, the considerable reduction of substances eluted from the photocurable resins into water after the post-curing process was verified by measuring the absorbance spectra. This result meant that our hypothesis is correct: unhardened monomers, photo-polymerization initiators and other low molecules stop eluting from the photocurable resins when they are post-cured.

Cytocompatibility was added to all three of the commercial epoxy-type photocurable resins by means of the same post-curing parameters. This test has thus shown that our post-curing process has general versatility and applicability for photocurable resins.

Embodiment 1

Three-dimensional cell culture wells were fabricated by microstereolithography. Specifically, cell culture wells measuring 16 mm and 15 mm in outside and inside diameter, respectively, 2 mm wall height, and 0.8 mm bottom thickness were fabricated. The materials used were SCR751 (glass transition temperature, 108° C.; D-Mec, Chuo-ku, Tokyo). The wells were exposed to a mercury xenon lamp (L2423, Hamamatsu Photonics, Hamamatsu City, Shizuoka Prefecture) for one hour to accelerate hardening. The wells were then heated under 18 different combined conditions of temperature (150° C., 175° C., and 200° C.) and time (0.5, 3, 6, 9, 12, and 24 hours). Rat adrenal pheochromocytoma cell line (PC12) was seeded in the wells, and the number of cells after 48 hours was counted and compared (FIG. 2). According to the result of the student's t-test, there was no significant difference between the ratio of the number of cells on the cell culture wells, which were heated at 200° C. for 6 hours or more, or at 175° C. for 24 hours, after 48 hours to the number of cells on said wells immediately after seeding, and the ratio of the number of cells separately cultured on commercial cell culture dishes after 48 hours to the number of cells on said dishes immediately after seeding. This relationship is shown by the asterisks in FIG. 3. This indicates that cytocompatibility was added to the cell culture wells fabricated by microstereolithography when the wells were heat treated at 200° C. for 6 hours or more.

Experiments were performed to confirm that the process of the present invention actually prevented elution of toxic substances from the cell culture wells fabricated by microstereolithography. Cell culture wells fabricated by microstereolithography and heat treated at 200° C. for 6 hours and those that were not heat treated were immersed in water for 40 hours. The absorption spectrum of the water in which these cell culture wells were immersed was measured using ultraviolet absorption spectroscopy. The result is shown in FIG. 3. As shown in FIG. 5, for the water in which the cell culture wells fabricated by unpost-baked microstereolithography were immersed, peaks were found on the absorption spectra at wavelengths of around 249 nm and around 200 nm (FIG. 5). These peaks were not found for the water in which the heat-treated cell culture wells were immersed (FIG. 5). This indicates that elution of toxic substances from said three-dimensional structures into water was prevented by the heat-treatment of the present invention.

For the purpose of verifying the effectiveness of the present invention for other photocurable resins, we studied the effects of the present invention on SCR11120 (glass transition temperature 43° C.; D-Mec) and SCR701 (81° C.; D-Mec), in addition to SCR751. These three types of resins were hardened using mercury xenon lamps and then heat treated at 200° C. for 6 hours. Cell culture tests were performed on these photocurable resins, and the effect of the present invention was confirmed.

As described in detail above, the present invention provides a general process to add cytocompatibility to microstereolithographic objects, and its efficacy was verified. It was also demonstrated that the microstereolithographic objects fabricated according to the present invention had almost the same cytocompatibility comparable with commercial cell culture dishes. It was clarified by ultraviolet absorption spectroscopy that the internal composition of the microstereolithographic object was changed in the post-curing process of the present invention, which explains why the cytotoxicity of the microstereolithographic object was reduced.

The present invention has been explained by citing working examples, but these embodiments are only a few examples and should not be construed as limiting.

INDUSTRIAL APPLICABILITY

The present invention can be applied to the design of tailor-made implant devices, and fabrication of cell devices set in three-dimensional alignment and microchemical devices including biochemical IC chips, which have not been achievable with conventional microstereolithography. The present invention would provide key technology to substantialize a new approach to microstereolithography in the biomedical field.

The invention claimed is:

1. A method for making a three-dimensional structure fabricated by microstereolithography, said method comprising steps of:
    forming said structure from a photo-curing material selected from a group consisting of acrylate, epoxy, acrylate-epoxy complex, and oxetane;
    detoxifying said structure sufficiently that it is possible to culture cells on a surface of and in contact with said structure;
    said detoxifying is achieved by heating said structure to at least its glass transition temperature after UV-curing,
    wherein one of dimensions x, y, and z of at least one portion of said structure is less than 1 mm; the method further comprising the step of
    deforming the structure due to its own weight by reducing its size according to size effect when the structure is heated above its glass transition temperature.

2. The method of making the three-dimensional structure as claimed in claim 1, wherein said detoxifying includes heating said structure to a temperature between about 175° C. to 200° C., for a heating time of 6 to 24 hours.

\* \* \* \* \*